United States Patent [19]

Skotnicki et al.

[11] Patent Number: 4,970,316

[45] Date of Patent: Nov. 13, 1990

[54] PYRANO-, THIOPYRANO-AND CYCLOHEXYLQUINOLINES AS INHIBITORS OF INTERLEUKIN 1

[75] Inventors: Jerauld S. Skotnicki, Chadds Ford; Steven C. Gilman, Berwyn, both of Pa.

[73] Assignee: American Home Products Corporation, New York, N.Y.

[21] Appl. No.: 347,317

[22] Filed: May 3, 1989

Related U.S. Application Data

[60] Division of Ser. No. 183,861, Apr. 20, 1988, Pat. No. 4,851,536, which is a continuation-in-part of Ser. No. 47,376, May 7, 1987, abandoned.

[51] Int. Cl.$^5$ ............... C07D 491/052; C07D 495/04; C07D 413/12; A61K 31/47
[52] U.S. Cl. ...................... 546/80; 544/126; 544/238; 544/284; 544/296; 544/333; 544/353; 544/361; 544/405; 546/89
[58] Field of Search ............... 546/80, 89; 514/291; 544/126, 361

[56] References Cited

U.S. PATENT DOCUMENTS

| | | | |
|---|---|---|---|
| 4,808,612 | 2/1989 | Skotnicki et al. | 514/290 |
| 4,816,464 | 3/1989 | Skotnicki et al. | 514/299 |
| 4,839,364 | 6/1989 | Shutske et al. | 546/93 |
| 4,843,079 | 6/1989 | Shutske et al. | 514/292 |
| 4,851,536 | 7/1989 | Skotnicki et al. | 546/106 |
| 4,868,177 | 9/1989 | Shutske et al. | 546/93 |

FOREIGN PATENT DOCUMENTS

| | | | |
|---|---|---|---|
| 183369 | of 1985 | European Pat. Off. | 546/142 |
| 443825 | of 1968 | Japan | 546/80 |
| 63264485 | of 1988 | Japan | 546/80 |

OTHER PUBLICATIONS

Nasi et al., "Synthesis of Pyrano—[4,3]—Quinolins", CA 89: 163459h (1978).

Primary Examiner—Mark L. Berch
Assistant Examiner—Celia Chang
Attorney, Agent, or Firm—George Tarnowski

[57] ABSTRACT

There are disclosed compounds of the formula

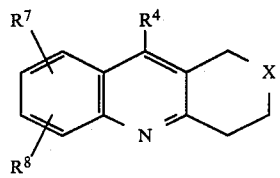

wherein
X is O, S, SO, SO$_2$ or CR$^1$R$^2$;
R$^1$ and R$^2$ are each independently hydrogen, lower alkyl, carboxyl, lower alkoxy carbonyl, lower cycloalkyl, phenyl, anphthyl, pyridyl, quinolinyl, pyrazinyl, pyridinyl, pyridazinyl, pyrimidinyl, quinoxalinyl, quinazolinyl or any of the foregoing aryl or hetaryl substituents substituted with halo, lower alkyl, lower alkyl carbonyl, benzoyl, COOR$^3$, OR$^3$, N(R$^3$)$_2$, CON(R$^3$)$_2$, SO$_3$R$^3$, SO$_2$N(R$^3$)$_2$, phenylsulfonyl, lower alkyl sulfonyl, cyano, nitro or trifluoromethyl;
R$^3$ is hydrogen, lower alkyl or phenyl;
R$^4$ is halo, morpholino, 4-methylpiperazino, R$^5$NNHR$^6$, R$^5$NCH$_2$CH$_2$OCH$_3$, or

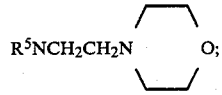

R$^5$ is hydrogen or lower alkyl;
R$^6$ is hydrogen, lower alkyl, lower alkanoyl, lower cycloalkyl or phenyl; and
R$^7$ and R$^8$ are each independently, hydrogen, halo, nitro, lower alkoxy, lower alkyl, cyano, trifluoromethyl, phenyl, carboxy or lower alkoxycarbonyl, with the proviso that when R$^1$ and R$^2$ are hydrogen or lower alkyl, R$^4$ is other than halo.

and, by virtue of their ability to inhibit interleukin 1, their use as antiinflammatory agents and in treatment of disease states involving enzymatic tissue destruction.

8 Claims, No Drawings

PYRANO-, THIOPYRANO- AND CYCLOHEXYLQUINOLINES AS INHIBITORS OF INTERLEUKIN 1

This is a division of U.S. Ser. No. 183,861 filed 4/20/88 now U.S. Pat. No. 4,851,536, which is a continuation-in-part of U.S. Ser. No. 047,376 filed 5/7/87 now abandoned.

This invention relates to novel compounds possessing interleukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.* 37, 173 (1986)]. IL 1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL 1 also stimulates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite, et al., *J. Exp. Med.*, 157, 801 (1983)]. Furthermore, IL 1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL 1 mediates acute phase reactions including alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory-/proliferative skin disorders as well as diseases in which the secretion of collagenase (and other tissue hydrolysing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain novel pyrano-, thiopyrano- and cyclohexyl- quinolines antagonize the activity of IL 1, and so are useful as antiinflammatory agents and in the treatment of pathologies whose etiology is collagenase-based tissue destruction. The present invention provides novel compounds having the formula:

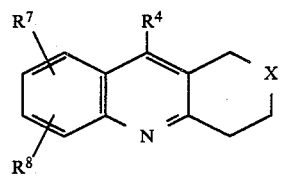

wherein
X is O, S, SO, $SO_2$ or $CR^1R^2$;
$R^1$ and $R^2$ are each independently hydrogen, lower alkyl, carboxyl, lower alkoxy carbonyl, lower cycloalkyl, phenyl, naphthyl, pyridyl, quinolinyl, pyrazinyl, pyridinyl, pyridazinyl, pyrimidinyl, quinoxalinyl, quinazolinyl or any of the foregoing aryl or hetaryl substituents substituted with halo, lower alkyl, lower alkyl carbonyl, benzoyl, $COOR^3$, $OR^3$, $N(R^3)_2$, $CON(R^3)_2$, $SO_3R^3$, $SO_2N(R^3)_2$, phenylsulfonyl, lower alkyl sulfonyl, cyano, nitro or trifluoromethyl;
$R^3$ is hydrogen, lower alkyl or phenyl;
$R^4$ is halo, morpholino, 4-methylpiperazino, $R^5NNHR^6$, $R^5NCH_2CH_2OCH_3$ or

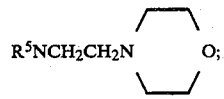

$R^5$ is hydrogen or lower alkyl;
$R^6$ is hydrogen, lower alkyl, lower alkanoyl, lower cycloalkyl or phenyl; and
$R^7$ and $R^8$ are each independently, hydrogen, halo, nitro, lower alkoxy, lower alkyl, cyano, trifluoromethyl, phenyl, carboxy or lower alkoxycarbonyl, with the proviso that when $R^1$ and $R^2$ are hydrogen or lower alkyl, $R^4$ is other than halo.

The terms "lower alkyl" and "lower alkoxy" refer to moieties having 1 to 6 carbon atoms in the carbon chain. The term "lower alkanoyl" refers to the moiety RCO— wherein R is an alkyl group having 1 to 6 carbon atoms. The term "lower cycloalkyl" refers to a saturated ring having 4 to 7 carbon atoms. The term "halo" refers to fluoro, chloro and bromo.

The especially preferred compounds are those having the formula

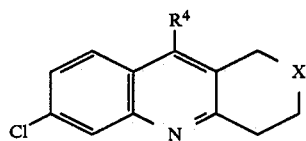

wherein

X is S, SO₂, CHCH₃ or

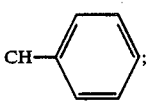

and
R⁴ is chloro or

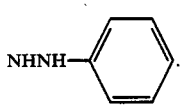

The compounds of the invention can be prepared by the reaction of a suitable cyclohexanone, tetrahydropyran-4-one or tetrahydrothiopyran-4-one with a suitably substituted amino benzoic acid in the presence of a halogenating agent to yield a halogenated intermediate:

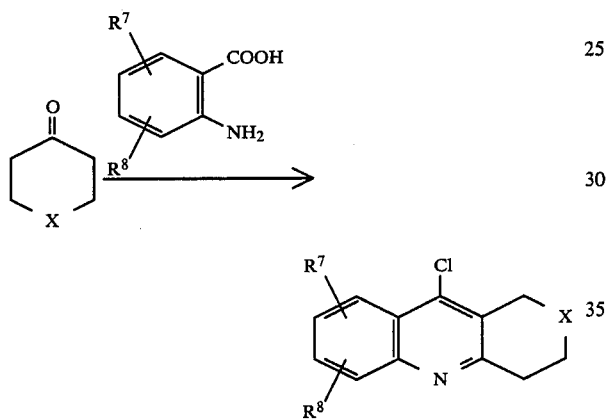

followed by reaction of the intermediate so obtained with a suitably substituted R⁴-containing reactant to yield the desired final product:

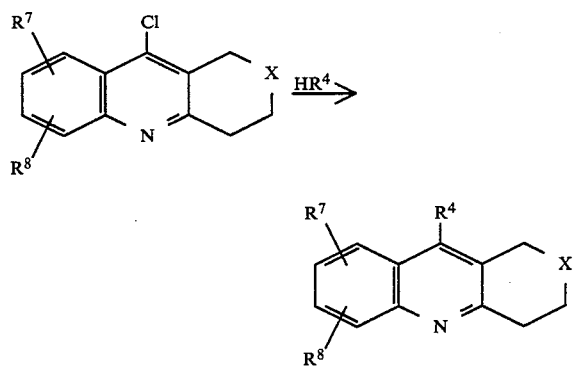

The starting materials used in the above outlined preparative sequences are all available commercially or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, peridontal disease, tumor invasiveness, corneal ulcerations, epidermolysis bullosa and the like.

When the compounds of the invention are employed as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The interleukin 1 antagonist activity of the compounds of the invention may be demonstrated by standard pharmacological procedures, which are described more fully in the examples given hereinafter.

These procedures illustrate the ability of the compounds of the invention to inhibit the IL1-induced release of neutral protease from articular chondrocytes.

The following examples show the preparation and pharmacological testing of compounds within the invention.

EXAMPLE 1

7-Chloro-3,4-dihydro-10-(2-phenylhydrazino)-1H-thiopyrano[4,3-b]quinoline

A.

7,10-Dichloro-3,4-dihydro-1H-thiopyrano[4,3-b]quinoline

To a slurry of 14.8 g (0.0863 mol) of 2-amino-4-chlorobenzoic acid and 150 ml of phosphorous oxychloride is added dropwise 10 g (0.086 mol) of tetrahydrothiopyran-4-one. The mixture is stirred at reflux for 3 hours and then concentrated in vacuo. The residue is dissolved in methylene chloride and added slowly to an ice-NH4OH mixture. The mixture is stirred for ½ hour and extracted with methylene chloride. The combined extracts are washed with water, dried over Na2SO4, and concentrated in vacuo to yield a dark solid. Trituration with ether furnishes 15 g (64%) of title compound: m.p. 112°-115° C.; IR (KBr) 1605, 1480, and 1415 cm$^{-1}$; NMR (CDCl3) δ8.08-8.02 (m, 2H), 7.58-7.52 (m, 1H), 4.08 (s, 2H), 3.44 (t, 2H), and 3.08 (t, 2H).

Analysis for: $C_{12}H_9NCl_2S$
Calculated: C, 53.34; H, 3.36; N, 5.19.
Found: C, 52.98; H, 3.51; N, 5.61.

B.
7-Chloro-3,4-dihydro-10-(2-phenylhydrazino)-1H-thiopyrano[4,3-b]quinoline

A mixture of 4.0 g (0.015 mol) of the compound of step A, above, 3.2 ml (0.03 mol) of phenylhydrazine, 2.5 ml of concentrated hydrochloric acid, and 150 ml of absolute ethanol is stirred under reflux for 6 hours. The precipitate, on cooling, is collected and dissolved in methanol. Treatment with a Na2CO3 solution yields an off-white solid. Recrystallization from toluene/hexane furnishes 575 mg (11%) of title compound: m.p. 201°-202° C.; IR 3300, 3240, 1605, and 1560 cm$^{-1}$; NMR (DMSO-d6) δ8.68-8.58 (m, 1H), 8.50 (s, 1H, exchangeable), 8.28 (s, 1H, exchangeable), 7.86-7.8 (m, 1H), 7.46-7.38 (m, 1H), 7.24-6.94 (m, 2H), 6.86-6.72 (m, 3H), 4.04 (s, 2H), 2.20 (t, 2H), and 1.96 (t, 2H).

Analysis for: $C_{18}H_{16}N_3ClS$
Calculated: C, 63.24; H, 4.72; N, 12.29.
Found: C, 63.59; H, 4.82; N, 11.93.

EXAMPLE 2

6-Chloro-1,2,3,4-tetrahydro-2-methyl-9-(2-phenylhydrazino)acridine

A. 6,9-Dichloro-1,2,3,4-tetrahydro-2-methylacridine, quarter hydrate

To a slurry of 15.3 g (0.0892 mol) of 2-amino-4-chlorobenzoic acid and 150 ml of phosphorous oxychloride is added dropwise 10 g (0.0892 mol) of 4-methylcyclohexanone. The mixture is stirred at reflux for 3 hours and then concentrated in vacuo. The residue is dissolved in methylene chloride and added slowly to an ice-NH4OH mixture. The mixture is stirred for ½ hour and extracted with methylene chloride. The combined extracts are washed with water, dried over Na2SO4, and concentrated in vacuo to yield a dark solid. Trituration with ether affords 14.2 g (60%) of title compound: m.p. 85°-87° C.; IR (KBr) 2920, 1605, 1585, 1480, and 1420 cm$^{-1}$; NMR (CDCl3) δ8.12-8.0 (m, 2H), 7.50-7.42 (m, 1H), 3.18-3.02 (m, 3H), 2.32-2.20 (m, 1H), 2.12-1.92 (m, 2H), 1.66-1.48 (m, 1H), and 1.2 (d, 3H).

Analysis for: $C_{14}H_{13}NCl_2 \cdot \frac{1}{4} H_2O$
Calculated: C, 62.12; H, 5.02; N, 5.18.
Found: C, 62.41; H, 4.92; N, 5.49.

B.
6-Chloro-1,2,3,4-tetrahydro-2-methyl-9-(2-phenylhydrazino)acridine

A mixture of 4.0 g (0.015 mol) of the compound of step A, above, 3.2 ml (0.03 mol) of phenylhydrazine, 2.5 ml of concentrated hydrochloric acid, and 150 ml of absolute ethanol is stirred under reflux for 6 hours. The precipitate, on cooling, is collected and dissolved in methanol. Treatment with a Na2CO3 solution yields an off-white solid. Recrystallization from toluene/hexane furnishes 1.1 g (22%) of title compound: m.p. 197°-199° C.; IR (KBr) 3330, 3240, 1605, 1555 and 1485 cm$^{-1}$; NMR (DMSO-d6) δ8.78-8.70 (m, 1H), 8.18 (s, 1H, exchangeable), 8.08 (s, 1H, exchangeable), 7.76-7.70 (m, 1H), 7.28-7.22 (m, 1H), 7.20-7.12 (m, 2H), 6.84-6.70 (m, 3H), 3.06-2.88 (m, 3H), 2.38-2.24 (m, 1H), 1.98-1.78 (m, 2H), 1.54-1.38 (m, 1H), and 1.08 (d, 3H).

Analysis for: $C_{20}H_{20}N_3Cl$
Calculated: C, 71.10; H, 5.97; N, 12.44.
Found: C, 71.12; H, 6.10; N, 12.09.

EXAMPLE 3

6-Chloro-1,2,3,4-tetrahydro-2-phenyl-9-(2-phenylhydrazino)acridine

A. 6,9-Dichloro-1,2,3,4-tetrahydro-2-phenylacridine, hemihydrate

To a slurry of 15 g (0.0874 mol) of 2-amino-4chlorobenzoic acid and 150 ml of phosphorous oxychloride is added dropwise 15 g (0.0871 mol) of 4-phenylcyclohexanone. The mixture is stirred at reflux for 3 hours and then concentrated in vacuo. The residue is dissolved in methylene chloride and added slowly to an ice-NH4OH mixture. The mixture is stirred for ½ hour and extracted with methylene chloride. The combined extracts are washed with water, dried over Na2SO4, and concentrated in vacuo to yield a dark solid. Trituration with ether provides 20 g (70%) of title compound: m.p. 134°-136° C.; IR 1605, 1585 and 1480 cm$^{-1}$; NMR (CDCl3) δ8.12-8.0 (m, 2H), 7.54-7.46 (m, 1H), 7.44-7.26 (m, 5H), 3.50-2.88 (m, 5H), and 2.28-2.02 (m, 2H).

Analysis for: $C_{19}H_{15}NCl_2 \cdot \frac{1}{2} H_2O$
Calculated: C, 67.66; H, 4.78; N, 4.15.
Found: C, 67.56; H, 4.57; N, 4.58.

B.
6-Chloro-1,2,3,4-tetrahydro-2-phenyl-9-(2-phenylhydrazino)acridine

A mixture of 5.22 g (0.0159 mol) of the compound of step A, above, 3.2 ml (0.03 mol) of phenylhydrazine, 2.5 ml of concentrated hydrochloric acid, and 150 ml of absolute ethanol is stirred under reflux for 6 hours. The precipitate on cooling is collected and dissolved in methanol. Treatment with Na2CO3 solution yields an off-white solid. Recrystallization from toluene/hexane furnishes 2.7 g (42%) of title compound: m.p. 198°-199° C.; IR (KBr) 3320, 3240, 1605, 1555 and 1485 cm$^{-1}$; NMR (DMSO-d6) δ8.84-8.76 (m, 1H), 8.22 (s, 1H, exchangeable), 8.16 (s, 1H, exchangeable), 7.78-7.72 (m, 1H), 7.46-7.12 (m, 8H), 6.87-6.70 (m, 3H), 3.28-2.74 (m, 5H), and 2.18-1.90 (m, 2H).

Analysis for: $C_{25}H_{22}N_3Cl$
Calculated: C, 75.08; H, 5.55; N, 10.51.
Found: C, 74.88; H, 5.60; N, 10.74.

EXAMPLE 4

10-Chloro-3,4-dihydro-1H-thiopyrano[4,3,-b]quinoline

A slurry of 10 g (0.0807 mol) of tetrahydrothiopyranone, 11.8 g (0.0807 mol) of anthranilic acid, and 150 ml of phosphorous oxychloride is stirred at 100° C. for 5 hours, cooled, and concentrated in vacuo. The residue is dissolved in methylene chloride and added slowly to an ice-NH4OH mixture. The aqueous phase is separated and extracted with methylene chloride. The combined organic phases are dried over Na2SO4 and concentrated in vacuo to give a waxy solid. Trituration with ethyl ether furnishes 11.2 g (59%) of the title compound: IR (KBr) 1575, 1550, and 1480 cm$^{-1}$; NMR (DMSO-d$_6$) δ8.18–7.66 (m, 4H), 4.04 (s, 2H), 3.30 (t, 2H), and 3.02 (t, 2H).

Analysis for: C$_{12}$H$_{10}$NSCl
Calculated: C, 61.14; H, 4.28; N, 5.94.
Found: C, 61.50; H, 4.39; N, 5.93.

EXAMPLE 5

3,4-Dihydro-10-(2-phenylhydrazino)-1H-thiopyrano[4,3-b]quinoline, three-quarters hydrate A mixture of 4.0 g (0.017 mol) of the compound of Example 4, 3.65 ml (3.68 g/0.034 mol) of phenylhydrazine, 150 ml of ethanol, and 2 ml of concentrated hydrochloric acid is stirred at reflux for 6 hours, then allowed to cool to ambient temperature. The resulting precipitate is dissolved in methanol and this solution is treated with Na$_2$CO$_3$ solution. The resulting precipitate is collected and triturated with ethyl ether to afford 980 mg (18%) of the title compound: IR (KBr) 3280, 3200, 1590, 1560, 1525, and 1490 cm$^{-1}$; NMR (DMSO-d$_6$) δ8.58–6.7 (complex m, 9H), 8.36 (br-s, 1H, exchangeable), 8.20 (br-s, 1H, exchangeable), 4.08 (s, 2H), 3.18 (t, 2H), and 2.94 (t, 2H).

Analysis for: C$_{18}$H$_{17}$N$_3$S·¾ H$_2$O
Calculated: C, 67.36; H, 5.81; N, 13.09.
Found: C, 67.36; H, 5.42; N, 12.77.

EXAMPLE 6

10-Chloro-3,4-dihydro-1H-thiopyrano[4,3-b]quinoline 2,2-dioxide

To a mixture of 3 g (0.0127 mol) of the compound of Example 4 and 100 ml of chloroform is added dropwise a solution of 6.04 g (0.028 mol) of m-chloroperoxybenzoic acid and 100 ml of chloroform. The reaction mixture is stirred for one hour, washed with Na$_2$CO$_3$ solution, dried over Na$_2$SO$_4$, and concentrated in vacuo to give a pasty solid. Trituration with ethyl ether furnishes 1.1 g (32%) of the title compound; IR (KBr) 1480, 1320, and 1120 cm$^{-1}$; NMR (DMSO-d$_6$) δ8.30–7.6 (complex m, 4H), 4.75 (s, 2H), 3.4–3.10 (complex m, 4H).

Analysis for: C$_{12}$H$_{10}$NClO$_2$S
Calculated: C, 53.83; H, 3.77; N, 5.23.
Found: C, 53.90; H, 3.83; N, 5.59.

EXAMPLE 7

7,10-Dichloro-3,4-dihydro-1H-thiopyrano[4,3-b]quinoline 2,2-dioxide

To a mixture of 3 g (0.0111 mol) of the compound of Example 1A, above, and 100 ml of chloroform is added dropwise a solution of 5.27 g (0.0244 mol) of m-chloroperoxybenzoic acid and 100 ml of chloroform. The reaction mixture is stirred for one hour, washed with Na$_2$CO$_3$ solution, dried over Na$_2$SO$_4$ and concentrated in vacuo to give a pasty solid. Trituration with ethyl ether affords 2.65 g (79%) of the title compound: IR (KBr) 1600, 1580, 1540, 1470, 1400, 1305, and 1120 cm$^{-1}$; NMR (DMSO-d$_6$) δ8.30–7.60 (m, 3H), 4.75 (s, 2H), and 3.40–3.05 (m, 4H).

Analysis for: C$_{12}$H$_9$NCl$_2$O$_2$S·¼ H$_2$O
Calculated: C, 46.99; H, 3.12; N, 4.57.
Found: C, 46.79; H, 3.09; N, 4.46.

EXAMPLE 8

7-Chloro-3,4-dihydro-10-(2-phenylhydrazino)-1H-thiopyrano[4,3-b]quinoline 2,2-dioxide To a solution of 110 mg (0.00032 mol) of the compound of Example 1B, above, and 25 ml of chloroform is added dropwise a solution of 185 mg (0.00087 mol) of m-chloroperoxybenzoic acid and 25 ml of chloroform. The reaction mixture is stirred for one hour, washed with Na$_2$CO$_3$ solution, dried over Na$_2$SO$_4$, and concentrated in vacuo. Trituration with ethyl ether affords 32 mg (27%) of the title compound: IR (KBr) 3400 (br), 3080, 3000, 1600, 1310, 1295, and 1130 cm$^{-1}$; NMR (DMSO-d$_6$) δ8.18–7.68 (m, 10H), 4.72 (s, 2H), 3.78–3.64 (m, 4H).

Analysis for: C$_{18}$H$_{16}$N$_3$ClSO$_2$
Calculated: C, 57.83; H, 4.31; N, 11.24.
Found: C, 58.46; H, 4.02; N, 10.96.

EXAMPLE 9

6,9-Dichloro-1,2,3,4-tetrahydro-2-acridinecarboxylic acid methyl ester

To a slurry of 16.5 g (0.096 mol) of 4-chloroanthranilic acid and 166 ml of phosphorous oxychloride is added portionwise 15 g (0.096 mol) of methyl 4-ketocyclohexane carboxylate. The reaction mixture is refluxed for 3 h, cooled, and concentrated in vacuo. The residue is dissolved in methylene chloride and poured into an ice-NH$_4$OH mixture. The aqueous phase is separated and extracted with methylene chloride. The combined organic phases are dried over Na$_2$SO$_4$ and concentrated in vacuo. The residue is triturated with ethyl ether to give 21.7 g (73%) of the title compound: IR (KBr) 1730, 1605, 1580, and 1550 cm$^{-1}$; NMR (DMSO-d$_6$) δ8.14–8.08 (m, 1H), 8.0–7.96 (m, 1H), 7.70–7.64 (m, 1H), 3.70 (s, 3H), 3.30–3.16 (m, 1H), 3.12–2.96 (m, 4H), 2.32–2.20 (m, 1H), and 2.04–1.86 (m, 1H).

Analysis for: C$_{15}$H$_{13}$Cl$_2$NO$_2$
Calculated: C, 58.08; H, 4.22; N, 4.52.
Found: C, 57.88; H, 4.41; N, 4.59.

EXAMPLE 10

6-Chloro-1,2,3,4-tetrahydro-9-(2-phenylhydrazino)-2-acridinecarboxylic acid ethyl ester A mixture of 11 g (0.035 mol) of the compound of Example 9, 7.1 g (0.066 mol) of phenylhydrazine, 5.5 ml of conc. hydrochloric acid, and 330 ml of ethanol is heated at reflux overnight. On cooling, the resulting precipitate is collected, and dissolved in methanol. This solution is treated with saturated Na$_2$CO$_3$ solution. The resulting solid is collected, washed with water and triturated with methylene chloride-ethyl acetate to give 5.7 g (41%) of solid. Recrystallization from isopropanol affords 794 mg (6%) of the title compound: mp 181°–182° C.; IR (KBr) 3320, 3240, 1720, 1605, and 1550 cm$^{-1}$; NMR (DMSO-d$_6$) δ8.24 (br-s, 1H, exchangeable), 8.18 (br-s, 1H, exchangeable), 7.32–7.22 (m, 1H), 7.20–7.16 (m, 3H), 6.86–6.68 (m, 4H), 4.10 (q, 2H), 3.16–2.80 (m, 5H), 2.20–2.06 (m, 1H), 1.96–1.84 (m, 1H), and 1.16 (t, 3H).

Analysis for: C$_{22}$H$_{22}$ClN$_3$O$_2$
Calculated: C, 66.74; H, 5.60; N, 10.62.
Found: C, 66.83; H, 5.48; N, 10.49.

EXAMPLE 11

6,9-Dichloro-1,2,3,4-tetrahydro-2-acridinecarboxylic acid

A mixture of 9.9 g (0.032 mol) of the compound of Example 9, 3.25 ml of ethanol, 32.5 ml of water, and 2.6 g of NaOH is stirred overnight at ambient temperature. The resulting solid is collected, washed with ethyl acetate, then dissolved in 100 ml of water. The solution is acidified with acetic acid and the resulting precipitate is collected, washed copiously with water and dried to give 6.64 g (70%) of the title compound: mp >250° C.; IR (KBr) 2900 (br), 2500 (br), 1700 (br), 1600, 1540, and 1470 cm$^{-1}$; NMR (DMSO-d$_6$) $\delta$12.6 (br-s, 1H, exchangeable), 7.92–7.86 (m, 1H), 7.82–7.76 (m, 1H), 7.54–7.48 (m, 1H), 3.10–2.76 (m, 5H), 2.28–2.12 (m, 1H), and 1.94–1.88 (m, 1H).

Analysis for: $C_{14}H_{11}Cl_2NO_2$
Calculated: C, 56.78; H, 3.74; N, 4.73.
Found: C, 56.85; H, 3.92; N, 4.82.

EXAMPLE 12

6-Chloro-1,2,3,4-tetrahydro-9-(2-phenylhydrazino)-2-acridinecarboxylic acid hemihydrate A mixture of 2.0 g (0.0051 mol) of the compound of Example 10, 6.4 ml of water, 6.4 ml of ethanol, and 0.4 g of NaOH is stirred at ambient temperature overnight, then concentrated in vacuo. The residue is dissolved in water and extracted with ethyl acetate. The aqueous phase is acidified using acetic acid and extracted with methylene chloride. The organic extracts are dried over Na$_2$SO$_4$, and concentrated in vacuo. The resulting powder is triturated with petroleum ether to give 42 mg of the title compound: IR (KBr) 3250 (br), 2940 (br), 2500 (br), 1700, and 1600 cm$^{-1}$; NMR (DMSO-d$_6$) $\delta$8.18–7.58 (m, 11H), 3.24–2.90 (m, 5H), 2.38–2.22 (m, 1H), and 2.10–1.98 (m, 1H).

Analysis for: $C_{20}H_{18}ClN_3O_2 \cdot \frac{1}{2} H_2O$
Calculated: C, 63.74; H, 5.08; N, 11.15.
Found: C, 63.57; H, 4.55; N, 10.59.

EXAMPLE 13

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 minutes at 37° C. in 0.05% hyaluronidase (Sigma H-3884), rinsed with HBSS and incubated with 0.2% trypsin (Sigma T-2395) for 10 minutes at 37° C. The slices are rinsed again and incubated for 10 minutes at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% CO$_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates (2×10$^5$ cells/well) and incubated at 37° C. until confluent (usually 4–6 days).

Stimulation of chondrocytes and drug treatment:

The confluent chondrocytes are rinsed twice with serum-free Ham's F-12 medium and 1 ml is added to each well. Fifty $\mu$l of purified human IL 1 (100 Units/ml; Genzyme Corporation, Boston, Mass.) is then added to stimulate these cells to secrete neutral protease. To measure drug effects, the cells are treated with test compound 10 minutes prior to addition of IL 1. The standard screening dose is 10 $\mu$M. Twenty-four hours after IL 1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 minutes at room temperature with 350 $\mu$M p-aminophenylmurcuric acetate to activate the latent enzyme. Three hundred $\mu$l of supernatant is then mixed with 500 $\mu$l of a 20 mg/ml suspension of azocoll and incubated at 37° C. for 18–24 hours with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

$$\% \text{ Inhibition of Protease Secretion} = \frac{(A_{520}) \text{ Untreated Supernatant} - A_{520} \text{ Drug treated Supernatant}}{A_{520} \text{ Untreated Supernatant}} \times 100$$

Where tested in this assay, the compounds of the invention gave the following results, showing them to exhibit a moderate to very significant inhibition of IL 1-induced protease secretion:

| Compound of Example No. | Dose ($\mu$M) | % Inhibition (I.S.D.) |
|---|---|---|
| 1A | 10 | 35 ± 11 |
| 1B | 10 | 98 ± 1 |
|  | 5 | 93 ± 5 |
|  | 1 | 94 |
|  | 0.1 | 67 |
| 2A | 10 | 34 ± 26 |
| 2B | 10 | 85 ± 6 |
|  | 1 | 36 |
| 3A | 10 | ≦20 |
| 3B | 10 | 81 ± 2 |
|  | 1 | 27 |
| 4 | 10 | 43 |
|  | 5 | 46 |
|  | 1 | 38 |
| 5 | 10 | 79 ± 14 |
|  | 5 | 55 ± 22 |
|  | 1 | 37 ± 0 |
| 6 | 10 | 32 |
|  | 5 | 19 |
| 7 | 10 | 25 |
|  | 5 | 26 |
|  | 1 | 10 |

-continued

| Compound of Example No. | Dose (μM) | % Inhibition (I.S.D.) |
|---|---|---|
| 8 | 10 | 16 |
|   | 5  | 37 |
|   | 1  | 3  |
| 9 | 10 | 58 |
|   | 5  | 53 |
|   | 1  | 30 |
| 10 | 10 | 96 |
|    | 1  | 91 |
|    | 0.1 | 70 |
| 11 | 10 | 88 |
|    | 1  | 50 |
|    | 0.1 | 58 |
| 12 | 10 | 68 |
|    | 1  | 61 |
|    | 0.1 | 57 |

What is claimed is:

1. A compound having the formula

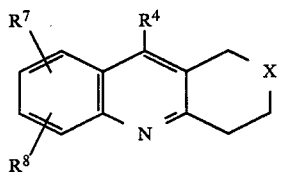

wherein
X is O, S, SO or $SO_2$;
$R^4$ is halo, morpholino, 4-methylpiperazino, $R^5NNHR^6$, or

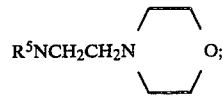

$R^5$ is hydrogen or lower alkyl;
$R^6$ is hydrogen, lower alkyl, lower alkanoyl, lower cycloalkyl or phenyl; and
$R^7$ and $R^8$ are each independently, hydrogen, halo, nitro, lower alkoxy, lower alkyl, cyano, trifluoromethyl, phenyl, carboxy or lower alkoxycarbonyl.

2. The compound of claim 1, having the name 7-chloro-3,4-dihydro-10-(2-phenylhydrazino)-1H-thiopyrano[4,3-b]quinoline.

3. The compound of claim 1, having the name 10-chloro-3,4-dihydro-1H-thiopyrano[4,3-b]quinoline.

4. The compound of claim 1, having the name 3,4-dihydro-10-(2-phenylhydrazino)-1H-thiopyrano[4,3-b]quinoline.

5. The compound of claim 1, having the name 10-chloro-3,4-dihydro-1H-thiopyrano[4,3-b]quinoline 2,2-dioxide.

6. The compound of claim 1, having the name 7,10-dichloro-3,4-dihydro-1H-thiopyrano[4,3-b]quinoline 2,2-dioxide.

7. The compound of claim 1, having the name 7-chloro-3,4-dihydro-10(2-phenylhydrazino)-1H-thiopyrano[4,3-b]quinoline 2,2-dioxide.

8. The compound of claim 1, having the name 7,10-dichloro-3,4-dihydro-1H-thiopyrano[4,3-b]quinoline.

* * * * *